(12) United States Patent
Zhu et al.

(10) Patent No.: US 7,838,110 B2
(45) Date of Patent: Nov. 23, 2010

(54) AZIRIDINE-FUNCTIONAL PHOTOACTIVE CROSSLINKING COMPOUNDS

(75) Inventors: Peiwang Zhu, Woodbury, MN (US); Maureen A. Kavanagh, Stanchfield, MN (US); Kelly S. Anderson, Houlton, WI (US); Larry R. Krepski, White Bear Lake, MN (US); Guy D. Joly, Shoreview, MN (US); Belma Erdogan, St. Paul, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 189 days.

(21) Appl. No.: 12/326,213

(22) Filed: Dec. 2, 2008

(65) Prior Publication Data

US 2010/0137469 A1 Jun. 3, 2010

(51) Int. Cl.
 C08J 133/04 (2006.01)
 C09D 203/04 (2006.01)
 C07C 49/00 (2006.01)
 C08G 73/00 (2006.01)

(52) U.S. Cl. .............................. 428/345; 428/355 AC; 522/39; 522/79; 522/84; 522/126; 548/967; 548/968; 548/969; 568/332; 568/335

(58) Field of Classification Search .................. 522/39, 522/84, 79, 126; 428/345, 355 AC; 548/967, 548/968, 969; 568/332, 335
See application file for complete search history.

(56) References Cited

U.S. PATENT DOCUMENTS

| 24,906 A | 12/1859 | Ulrich |
| 4,062,886 A | 12/1977 | Turner |
| 4,181,755 A | 1/1980 | Liu et al. |
| 4,243,500 A | 1/1981 | Glennon |
| 4,303,485 A | 12/1981 | Levens |
| 4,304,705 A | 12/1981 | Heilmann et al. |
| 4,364,972 A | 12/1982 | Moon |
| 4,619,979 A | 10/1986 | Kotnour et al. |
| 4,777,276 A | 10/1988 | Rasmussen et al. |
| 4,843,134 A | 6/1989 | Kotnour et al. |
| 5,506,279 A | 4/1996 | Babu et al. |
| 5,532,112 A * | 7/1996 | Kohler et al. ............ 430/281.1 |
| 5,741,543 A * | 4/1998 | Winslow et al. .......... 427/208.4 |
| 5,753,768 A | 5/1998 | Ellis |
| 5,773,485 A | 6/1998 | Bennett et al. |
| 5,902,836 A * | 5/1999 | Bennett et al. ................. 522/8 |
| 6,245,922 B1 | 6/2001 | Heilmann et al. |
| 6,294,249 B1 | 9/2001 | Hamer et al. |
| 6,734,256 B1 | 5/2004 | Everaerts et al. |
| 7,276,247 B2 | 10/2007 | Fansler et al. |
| 7,459,489 B2 * | 12/2008 | Lewandowski et al. ...... 522/181 |
| 7,612,122 B2 * | 11/2009 | Herlihy et al. .............. 522/150 |
| 7,652,103 B2 * | 1/2010 | Kavanagh et al. ......... 525/329.9 |
| 7,691,915 B2 * | 4/2010 | Kim et al. ...................... 522/28 |
| 2007/0213463 A1 * | 9/2007 | Sherman et al. ............. 525/100 |
| 2007/0299211 A1 * | 12/2007 | Chen et al. ................ 525/329.7 |
| 2009/0246390 A1 * | 10/2009 | Krepski et al. ............ 427/385.5 |

FOREIGN PATENT DOCUMENTS

| DE | 2630784 | 2/1977 |
| WO | WO 95/10552 | 4/1995 |
| WO | WO 97/05100 | 2/1997 |
| WO | WO 2005/092403 | 10/2005 |
| WO | WO 2008/100713 | 8/2008 |
| WO | WO 2008/100755 | 8/2008 |
| WO | WO 2009/102623 | 8/2009 |
| WO | WO 2009/120420 | 10/2009 |

OTHER PUBLICATIONS

PCT International Search Report, PCT/US2009/065447.
Iwakura et al., "A Novel Preparation of Pseudoxzaolones," Tetraheron, vol. 23, pp. 3363-3373, Pergamon Press Ltd., (1967).
Hubner et al., Makromolekulare Chem., vol. 11, No. 124, pp. 109-124, (1970).
Taylor et al., Journal of Polymer Science, Polymer Letters., vol. 7, pp. 597-603, (1969).
"Effect of Asymmetric Centers on Free Radical Polymerization and the Properties of Polymers: Methacrylyl Alanine, Methacrylyl Glutamic Acid, Acrylyl Glutamic Acid, and Their Polymers," Journal of Polymer Science, vol. 54, pp. 491-503, (1961), Kulkarni et al.

* cited by examiner

*Primary Examiner*—Susan W Berman
(74) *Attorney, Agent, or Firm*—Kent S. Kokko

(57) ABSTRACT

A photoactive compound that is the Michael addition reaction product of an aziridine compound and a photoinitiator-functional (meth)acrylate is described. The compound can be used to crosslink (meth)acrylic polymers via a hydrogen abstracting or an alpha-cleavage mechanism.

26 Claims, No Drawings

AZIRIDINE-FUNCTIONAL PHOTOACTIVE CROSSLINKING COMPOUNDS

FIELD OF THE INVENTION

This invention relates to photoactive crosslinking compounds that may be compounded with (meth)acrylic copolymers and photoactivated by actinic radiation to crosslink such copolymers.

BACKGROUND INFORMATION

Pressure sensitive adhesives (PSAs) made by photopolymerizing an alkyl acrylate and a polar copolymerizable monomer are known in the art. See, e.g., U.S. Pat. Nos. RE 24,906, 4,181,755, 4,364,972, and 4,243,500. Acrylic-based PSAs exhibit good adherence to high energy (i.e. polar) substrates.

Solvent-processed acrylic PSA compositions can be crosslinked by adding a polyfunctional crosslinking compound that reacts with a reactive group present in the polymer. Hot melt coating a PSA composition eliminates the necessity of solvent processing. To hot melt process an adhesive composition, the composition must not be crosslinked before and during the coating process; however, to achieve a PSA with balanced properties (i.e., peel and shear adhesion), the composition eventually must be crosslinked. In hot melt coating processes, this is usually done by exposure to high energy radiation (e.g., E-beam or high intensity ultraviolet radiation). Commonly, when high intensity ultraviolet radiation is used, a photoactive crosslinking species such as benzophenone is added to the composition.

Another method of photocrosslinking involves incorporating monomer units including pendent photoinitiator groups into the polymer backbone prior to coating. Such polymers can be coated and subsequently cured by conventional irradiation techniques. This process is described in U.S. Pat. No. 7,276,247 (Fansler et al.).

SUMMARY OF THE INVENTION

Briefly, the present disclosure provides photoactive crosslinking compound having the general formula:

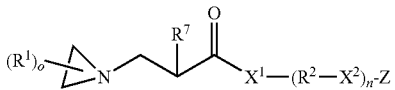

wherein $R^1$ is H or a $C_1$ to $C_4$ alkyl group, preferably $CH_3$;
o is 0 to 2, preferably 1;
$X^1$ and $X^2$ are each —O— or —NH—;
$R^2$ is a divalent alkylene of 2 to 10 carbon atoms or —$(R^3)_2C$ $(CH_2)_m(CO)OR^9$—, where m is 0 or 1, $R^3$ is H or a $C_1$ to $C_4$ alkyl group, and $R^9$ is a $C_2$-$C_6$ alkylene;
n is 0 or 1, preferably 1;
$R^7$ is H or $CH_3$; and
Z is a photoinitiator group.

In another aspect, the present disclosure provides a crosslinkable composition comprising an acid-functional (meth)acrylate copolymer and a photoactive crosslinking compound of Formula I. The crosslinkable composition may be a solution polymer, emulsion polymer or a syrup polymer.

The present disclosure further provides a method of preparing the photoactive crosslinking compound comprising the step of reacting an aziridine compound by Michael addition to an acryloyl compound:

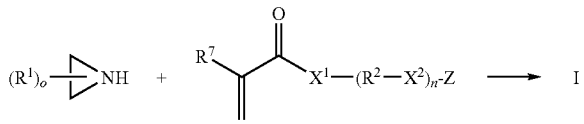

wherein $R^1$, o, $X^1$, $X^2$, $R^2$, $R^7$, n and Z are as defined for Formula I.

In another aspect, the present disclosure provides a method of making the above photoactive crosslinking compound comprising the step of reacting a 2-alkenyl azlactone compound and a nucleophilic photoinitiator compound, which may include acetophenone, benzophenone, anthraquinone, 9-fluorenone, anthrone, xanthone, thioxanthone, acridone, dibenzosuberone, benzil, or chromone compounds, having a nucleophilic group. This reaction can be facilitated by the addition of a catalyst comprising a nitrogen-containing base, preferably a bicyclic amidine or guanidine, or a trivalent phosphorous compound.

One of two broad categories of photoactive crosslinking agents are generally used to photocrosslink acrylic PSA compositions: an α-cleaving agent or a hydrogen abstracting agent. Of the latter category, the most commonly used example is probably acryloylbenzophenone (ABP). This compound is an efficient crosslinker, but it is not always soluble in the relatively non-polar monomers that make up PSA monomer formulations. Additionally, acryloylbenzophenone must be incorporated during polymerization of the acrylate adhesive polymer composition, limiting the flexibility of ABP, as different polymers must be prepared to accommodate different levels of the ABP crosslinking agent. Crosslinking agents such as ABP are further limited by the reactivity toward the component monomers of acrylic adhesive polymers, resulting in unpredictable distribution of the ABP monomer units in the polymer chain.

In contrast, the instant photoactive crosslinking compounds are incorporated into an acid functional (meth)acrylate polymer by ring opening addition of the aziridine group by an acid functional group of the polymer. Therefore the instant photoactive crosslinking compounds can be added in any desired amounts to either the extant polymer or the syrup polymer. The different mechanism of incorporation results in a different distribution of the crosslinking compounds in the polymer chain, and different performance of the resulting adhesives.

DETAILED DESCRIPTION OF PREFERRED EMBODIMENTS

The photoactive crosslinking compound of the present disclosure has the general formula:

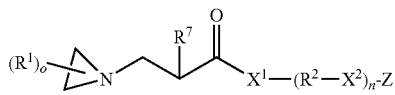

wherein $R^1$ is H or a $C_1$ to $C_4$ alkyl group, preferably $CH_3$;
o is 0 to 2;
$X^1$ and $X^2$ are each —O— or —NH—;

$R^2$ is a divalent alkylene of 2 to 10 carbon atoms or —$(R^3)_2C(CH_2)_m(CO)OR^9$—, where m is 0 or 1, $R^3$ is H or a $C_1$ to $C_4$ alkyl group, and $R^9$ is a $C_2$-$C_6$ alkylene;

n is 0 or 1, $R^7$ is H or $CH_3$; and

Z is a photoinitiator group.

In one embodiment, the $R^2$ group is a divalent alkylene group having 2 to 10 carbon atoms, said divalent alkylene being linear or branched, providing photoactive crosslinking compounds of the formula:

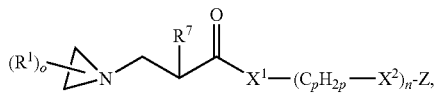
II where $R^1$ is H or a $C_1$ to $C_4$ alkyl group;

o is 0 to 2;

$X^1$ and $X^2$ are independently —O— or —NH—;

p is 2 to 10, preferably 2 to 6, n is 0 or 1;

$R^7$ is H or $CH_3$; and

Z is a photoinitiator group.

In another embodiment, the $R^2$ group is derived from the ring opening of an azlactone compound, providing photoactive crosslinking compounds of the formula:

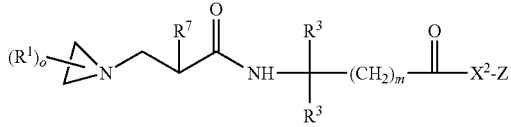
III wherein $R^1$ is H or a $C_1$ to $C_4$ alkyl group;

o is 0 to 2;

$R^3$ is H or $CH_3$;

x2 is —O— or —NH—;

m is 0 or 1, $R^7$ is H or $CH_3$; and

Z is a photoinitiator group.

The photoinitiator group may be of the hydrogen-abstraction type or the α-cleavage type.

In one embodiment, Z can be a radiation sensitive aryl ketone group capable of Norrish Type I cleavage (α-cleavage). Such α-cleavage photoinitiator groups are particularly suited for syrup polymer compositions. Basic photochemistry of aryl ketones is discussed in a text by J. G. Calvert and J. N. Pitts, Jr., "Photochemistry" John Wiley & Sons, Inc., New York (1966). Preferably Z is selected from radiation sensitive groups having the formula:

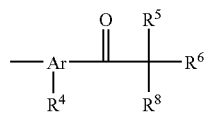

in which Ar is an arylene group having 6 to 12 carbon atoms that can be substituted by a lower alkyl group having one to six carbon atoms, Ar preferably is selected from phenylene, naphthalenylene, and biphenylene; and $R^4$ is selected from the group consisting of hydrogen, $C_1$ to $C_{12}$ alkyl groups, $C_1$ to $C_{12}$ alkoxy groups, and phenyl groups;

$R^5$, $R^6$, and $R^8$ independently are selected from the group consisting of hydroxyl, $C_1$ to $C_{12}$ alkyl groups, $C_1$ to $C_{12}$ alkoxy groups, di($C_1$ to $C_{12}$ alkyl substituted) amino groups, and aryl groups, provided that at least one of $R^5$, $R^6$ and $R^8$ is selected from the group consisting of hydroxyl, $C_1$ to $C_{12}$ alkoxy groups, or di $C_1$ to $C_{12}$ alkyl substituted amino groups, or that any two of $R^5$, $R^6$, and $R^8$ together can be an alkylene group, —$(C_qH_{2q})$—, or an alkylenedioxy group, —O—$(C_qH_{2q})$—O—, in which q is an integer having a value of two or three, that together with the carbon atoms to which they are attached to form a 5- or 6-membered ring, or any two of $R^5$, $R^6$, and $R^8$ taken together with the carbon atom to which they are attached can form a carbonyl group —CO— provided that the remaining $R^5$, $R^6$, and $R^8$ is selected from the group consisting of hydroxyl, $C_1$ to $C_{12}$ alkoxy groups, di $C_1$ to $C_{12}$ alkyl substituted amino groups, and aryl groups.

Examples of α-cleavage photoinitiator groups corresponding to Z may be represented by the following structures. Such groups are substituted with the —$(X^2$—$R^2)_n$—$X^1$—H at the open valence and preferably n is 1.

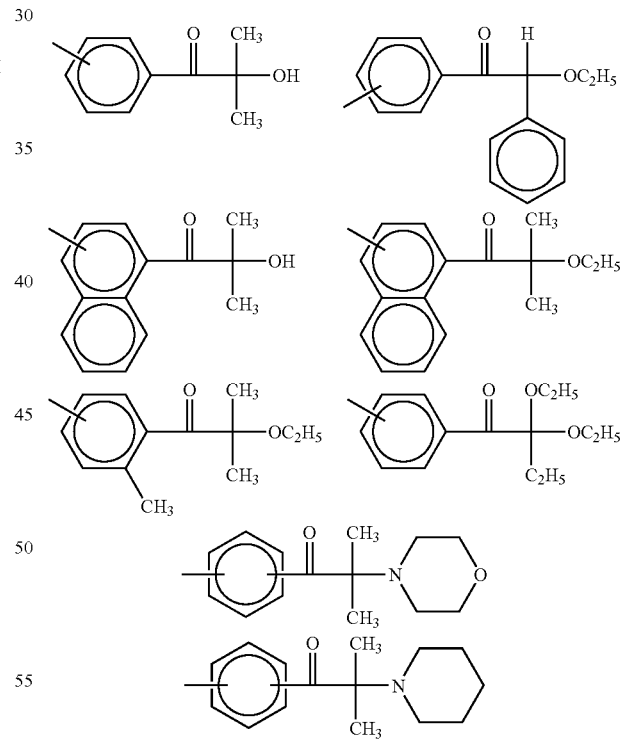

In another embodiment the photoinitiator group Z may be selected from a hydrogen abstraction-type photoinitiator group. Such groups may be derived from a benzophenone, anthraquinone, 9-fluorenone, anthrone, xanthone, thioxanthone, acridone, dibenzosuberone, chromone, flavone, benzyl, and acetophenone compounds substituted by a nucleophilic H—$X^1$—$(R^2$—$X^2)_n$— group at the open valence. Such groups may be represented by:

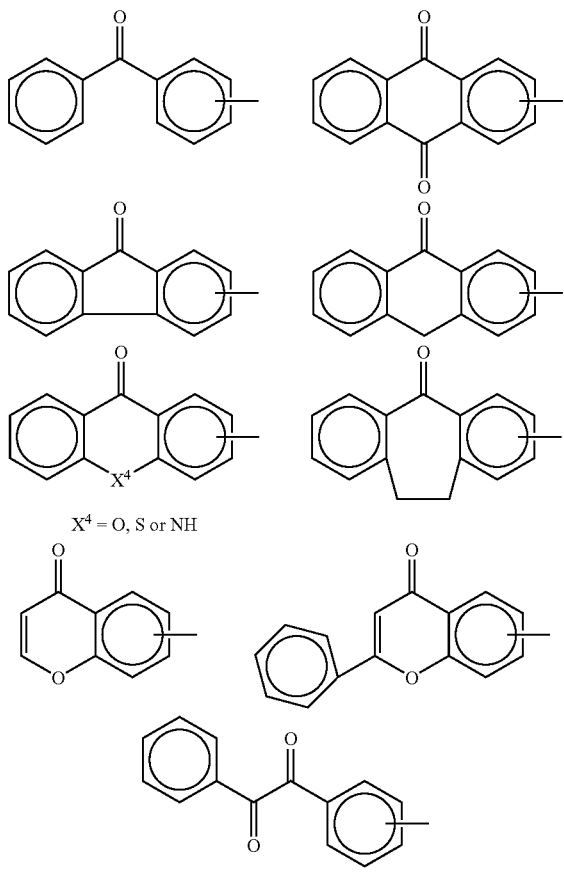

X⁴ = O, S or NH

In general, the photoactive compounds of Formulas I-II may be prepared by a Michael addition reaction of an aziridine compound to an acryloyl compound having a photoinitiator group:

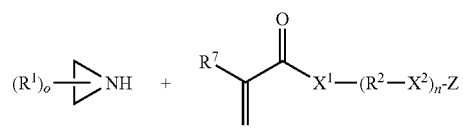

The acryloyl compound, in turn, may be prepared by acylation of a photoinitiator compound having a nucleophilic group:

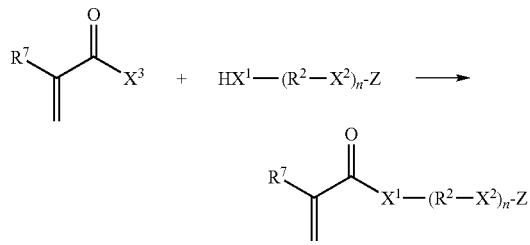

where $X^3$ is a leaving group, such as a halide or alkoxy, that may be displaced by the $HX^1$—, $X^1$ and $X^2$ are independently —O— or —NH—;
$R^2$ is a divalent alkylene of 2 to 10 carbon atoms or —$(R^3)_2$C$(CH_2)_m(CO)OR^9$—, where m is 0 or 1, $R^3$ is H or a $C_1$ to $C_4$ alkyl group, and $R^9$ is a $C_2$-$C_6$ alkylene;
$R^7$ is H or $CH_3$; and
Z is a photoinitiator group.

The photoactive crosslinking compound of Formula III can be prepared by the ring-opening of an electrophilic 2-alkenyl azlactone compound with a nucleophilic H—$X^1$—($R^2$—$X^2$)$_n$— group substituted photoinitiator compound. Reference may be made to U.S. Pat. No. 5,505,279 (Gaddam et al.). Suitable nucleophiles include hydroxyl, primary amine, secondary amine, and thiol groups. This ring opening is followed by the Michael addition reaction of an aziridine compound with the ring-opened intermediate:

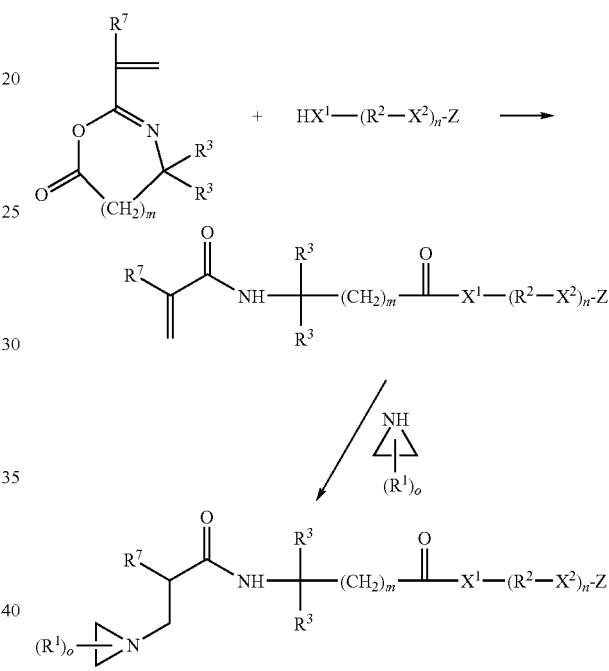

wherein
$R^1$ is H or a $C_1$ to $C_4$ alkyl group;
o is 0 to 2;
$R^3$ is H or $CH_3$;
$X^2$ is —O— or —NH—;
m is 0 or 1,
$R^7$ is H or $CH_3$; and
Z is a photoinitiator group.

A significant advantage of using the 2-alkenyl azlactone instead of acryloyl chloride as an acylating agent is that the azlactone nucleophile reaction involves ring-opening addition; no smaller by-product molecule (such as hydrogen chloride) is displaced or generated in the reaction.

Alkenyl azlactones can be prepared by methods well known in the art. See, e.g., Iwakura et al., *Tetrahedron,* 23, 3363 (1967); Hubner et al., *Makromol. Chem.,* 11, 109 (1970); Taylor et al., *J. Poly. Sci., Poly. Let. Ed.,* 7, 597 (1969); and U.S. Pat. Nos. 4,304,705 and 4,777,276. These methods involve subjecting an amino acid having the general formula $H_2N(CH_2)_mC(R^3)_2COOH$ (wherein m and $R^3$ are defined as above) to acylation with an ethylenically unsaturated acylating agent having the general formula $H_2C=CR^7C(O)Cl$ (wherein $R^7$ is defined as above) using the method described by, for example, Kulkari et al., *J. Poly. Sci.*, 54, 491 (1961) in which the acylating agent (preferably containing a polymerization inhibitor such as hydroquinone) and an equivalent amount of an acid absorber (e.g., aqueous NaOH) are added portionwise to a chilled (e.g., 0° C.), vigorously stirred aqueous solution of an equimolar amount of an alkali metal salt of the amino acid, followed by neutralization with an aqueous acid (e.g., 6 N HCl), and isolation of the unsaturated peptide carboxylic acid product. This product is then dehydrated by introduction of a dehydrating agent (such as, for example, acetic anhydride, ethyl chloroformate, or dicyclohexylcarbodiimide) to give a 2-alkenyl azlactone.

Because of the wider availability of starting amino acids and their greater thermodynamic stability (reflected in higher synthetic yields), the 5-membered ring species are preferred. Examples of suitable 5-membered ring azlactones include 2-ethenyl-1,3-oxazolin-5-one; 2-ethenyl-4-methyl-1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-4-methyl-4-ethyl-1,3-oxazolin-5-one; 2-ethenyl-4,4-dibutyl-1,3-oxazolin-5-one; 2-isopropenyl-4-butyl-1,3-oxazolin-5-one; and 2-isopropenyl-4-propyl-1,3-oxazolin-5-one, although other such compounds will be apparent to those skilled in the art. Preferred azlactones are 2-ethenyl-4,4-dimethyl-1,3-oxazolin-5-one and 2-isopropenyl-4,4-dimethyl-1,3-oxazolin-5-one.

Nucleophile substituted photoinitiator compounds that can be used in the present disclosure include benzophenone, anthraquinone, 9-fluorenone, anthrone, xanthone, thioxanthone, acridone, dibenzosuberone, chromone, flavone, benzyl, and acetophenone compounds having a nucleophilic H—$X^1$—($R^2$—$X^2$)$_n$— group thereon. This may be exemplified by the benzophenone compound:

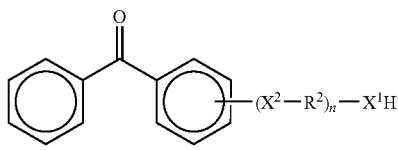

The ring-opening reaction of the electrophilic azlactone compound and the nucleophile-substituted photoinitiator compound can be catalyzed by nitrogen-containing bases, such as bicyclic amidines and guanidines, or trivalent phosphorus compounds. When used, the amount of catalyst utilized in the instant process can vary from about 0.1 mole percent (based on the amount of azlactone present) to about 50 mole percent or more. However, 0.5 to 5 mole percent is sufficient to provide a reasonable reaction rate in most instances.

The photoactive crosslinking compounds of the present disclosure can be used in the preparation of adhesives, including hot-melt and pressure-sensitive adhesives. This can be accomplished by mixing from about 0.01 to about 5 parts by weight (pbw) of a photoactive crosslinking compound into 95 to 99.99 pbw of acid-functional (meth)acrylate copolymer. This can be done in either the extant polymer or the partially polymerized monomer-polymer syrup.

The present disclosure provides a pre-adhesive composition comprising an acid-functional (meth)acrylate copolymer and an aziridine crosslinking compound of Formulas I-III, which when polymerized and/or crosslinked, provides a pressure-sensitive adhesive and pressure-sensitive adhesive articles.

The (meth)acrylate ester monomer useful in preparing the acid functional (meth)acrylate adhesive copolymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 3,7-dimethylheptanol, 3,7-dimethylhept-3-eneol, 1-decanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable source, such as 2-octanol, citronellol, dihydrocitronellol.

The (meth)acrylate ester monomer is present in an amount of 85 to 99 parts by weight based on 100 parts total monomer content used to prepare the polymer. Preferably (meth)acrylate ester monomer is present in an amount of 90 to 95 parts by weight based on 100 parts total monomer content.

The polymer further comprises an acid functional monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof Examples of such compounds include those selected from acrylic acid, methacrylic acid, itaconic acid, fumaric acid, crotonic acid, citraconic acid, maleic acid, oleic acid, β-carboxyethyl(meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids may be used. The acid functional monomer is generally used in amounts of 1 to 15 parts by weight, preferably 1 to 10 parts by weight, based on 100 parts by weight total monomer.

The polar monomers useful in preparing the copolymer are both somewhat oil soluble and water soluble, resulting in a distribution of the polar monomer between the aqueous and oil phases in an emulsion polymerization. Useful polar monomers are non-acid functional.

Representative examples of suitable polar monomers include but are not limited to 2-hydroxyethyl(meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl)(meth)acrylates including 2-(2-ethoxyethoxy)ethyl(meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof Preferred polar monomers include those selected from the group consisting of 2-hydroxyethyl (meth)acrylate and N-vinylpyrrolidinone. The polar monomer may be present in amounts of 0 to 10 parts by weight, preferably 1 to 5 parts by weight, based on 100 parts by weight total monomer.

When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. Such vinyl monomers are generally used at 0 to 5 parts by weight, preferably 1 to 5 parts by weight, based on 100 parts by weight total monomer.

In order to increase cohesive strength of the coated adhesive composition, a multifunctional (meth)acrylate may be incorporated into the blend of polymerizable monomers. Multifunctional acrylates are particularly useful for emulsion or syrup polymerization. Examples of useful multifunctional (meth)acrylate include, but are not limited to, di(meth)acrylates, tri(meth)acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof The amount and identity of multifunctional (meth)acrylate is tailored depending upon application of the adhesive composition. Typically, the multifunctional (meth)acrylate is present in amounts less than 5 parts based on total dry weight of adhesive composition. More specifically, the crosslinker may be present in amounts from 0.01 parts to 1 part based on 100 parts total monomers of the adhesive composition.

The copolymerizable monomer mixture may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The emulsion mixture may further comprise up to about 0.5 parts by weight of a chain transfer agent, typically about 0.01 to about 0.5 parts by weight, if used, preferably about 0.05 parts by weight to about 0.2 parts by weight, based upon 100 parts by weight of the total monomer mixture.

The acid-functional acrylate copolymers herein can be prepared by any conventional free radical polymerization method, including solution, radiation, bulk, dispersion, emulsion, and suspension processes. The initiator used in preparing the copolymers (or syrup polymers) may be a photo- or thermal initiator, and such initiators may be oil- or water soluble.

Water-soluble and oil-soluble initiators useful in preparing the acid-functional acrylate copolymers are initiators that, on exposure to heat or radiation, generate free-radicals which initiate (co)polymerization of the monomer mixture. Water-soluble initiators are preferred for preparing the (meth)acrylate polymers by emulsion polymerization.

Suitable water-soluble initiators include but are not limited to those selected from the group consisting of potassium persulfate, ammonium persulfate, sodium persulfate, and mixtures thereof, oxidation-reduction initiators such as the reaction product of the above-mentioned persulfates and reducing agents such as those selected from the group consisting of sodium metabisulfite and sodium bisulfite; and 4,4'-azobis(4-cyanopentanoic acid) and its soluble salts (e.g., sodium, potassium). The preferred water-soluble initiator is potassium persulfate. Suitable oil-soluble initiators include but are not limited to those selected from the group consisting of azo compounds such as VAZO™ 64 (2,2'-azobis(isobutyronitrile)), VAZO™ 67 (2,2'azobis (2-methylbutyronitrile)), and VAZO™ 52 (2,2'-azobis(2,4-dimethylpentanenitrile)), available from E.I. du Pont de Nemours Co., peroxides such as benzoyl peroxide and lauroyl peroxide, and mixtures thereof. The preferred oil-soluble thermal initiator is 2,2'-azobis(2,4-dimethylpentanenitrile). When used, initiators may comprise from about 0.05 to about 1 part by weight, preferably about 0.1 to about 0.5 part by weight based on 100 parts by weight of monomer components in the pressure sensitive adhesive.

Depending upon the method of polymerization, the pre-adhesive composition may include an appropriate initiator. For polymerization by ultraviolet light, a photoinitiator is included. Useful photoinitiators include substituted acetophenones such as benzyl dimethyl ketal and 1-hydroxy-cyclohexyl phenyl ketone, substituted alpha-ketols such as 2-methyl-2-hydroxypropiophenone, benzoin ethers such as benzoin methyl ether, benzoin isopropyl ether, substituted benzoin ethers such as anisoin methyl ether, aromatic sulfonyl chlorides, and photoactive oximes. The photoinitiator may be used in an amount from about 0.001 to about 5.0 parts by weight per 100 parts of total monomer (or polymer), preferably from about 0.01 to about 5.0 parts by weight per 100 parts of total monomer, and more preferably in an amount from 0.1 to 0.5 parts by weight per 100 parts of total monomer.

In one embodiment the present disclosure provides method of preparing a pressure sensitive adhesive comprising partially polymerizing monomers to produce a syrup polymer comprising the acid functional (meth)acrylate copolymer and unpolymerized monomers. Generally, the crosslinking compound is added to the partially polymerized composition (the syrup polymer), coated on a suitable substrate and further polymerized and crosslinked by exposure to UV radiation. The crosslinking compound may be added to the syrup polymer in amounts of 0.01 to 5 parts by weight, preferably 0.1 to 1 parts by weight, based of 100 parts by weight of acid functional (meth)acrylate copolymer syrup. The photoinitiator group Z of Formula I is preferably selected as α-cleavage type photoinitator to the efficiently polymerize the monomers and crosslink the resulting polymer.

Partial polymerization provides a coatable solution of the acid functional (meth)acrylate solute copolymer in one or more solvent monomers. For syrup application processing, a preferred monomer mixture (second component) comprises 85 to 99 pbw of one or more (meth)acrylate ester monomers, 1 to 15 pbw of acid functional monomers, 0 to 10 pbw of one or more second, non-acid, polar monomers, and 0 to about 5 pbw of other vinyl monomers, based on 100 parts total monomer.

Once compounded with the photoactive crosslinking compound of Formula I, the syrup is coated on suitable substrates. The coating on the web may be irradiated with activating UV radiation to polymerize the monomer component(s) and crosslink the co-polymers. The crosslinking compound may be added to the polymer in amounts of 0.01 to 1 parts by weight, preferably 0.1 to 0.5 parts by weight, based of 100 parts by weight of acid functional (meth)acrylate syrup copolymer.

UV light sources can be of two types: 1) relatively low light intensity sources such as Blacklights which provide generally 10 mW/cm$^2$ or less (as measured in accordance with procedures approved by the United States National Institute of Standards and Technology as, for example, with a UVI-MAP™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm$^2$, preferably between 15 and 450 mW/cm$^2$. Where actinic radiation is used to fully or partially polymerize the syrup polymer composition, high intensities and short exposure times are preferred. For example, an intensity of 600 mW/cm$^2$ and an exposure time of about 1 second may be used successfully. Intensities can range from about 0.1 to about 150 mW/cm$^2$, preferably from about 0.5 to about 100 mW/cm$^2$, and more preferably from about 0.5 to about 50 mW/cm$^2$.

The degree of conversion can be monitored during the irradiation by measuring the index of refraction of the polymerizing medium as previously described. Useful coating viscosities are achieved with conversions (i.e. the percentage of available monomer polymerized) in the range of up to 30%, preferably 2-20%, more preferably from 5-15%, and most preferably from 7-12%. The molecular weight (weight average) of the solute polymer(s) is at least 100,000, preferably at least 500,000.

When preparing adhesives, it is expedient for the photoinitiated polymerization reactions to proceed to virtual completion, i.e., depletion of the monomeric components, at temperatures less than about 70° C. (preferably at 50° C. or less) with reaction times less than 24 hours, preferably less than 12 hours, and more preferably less than 6 hours. These temperature ranges and reaction rates obviate the need for free radical polymerization inhibitors, which are often added to acrylic systems to stabilize against undesired, premature polymerization and gelation. Furthermore, the addition of inhibitors adds extraneous material that will remain with the system and inhibit the desired polymerization of the syrup polymer and formation of the crosslinked pressure sensitive adhesives of the invention. Free radical polymerization inhibitors are often required at processing temperatures of 70° C. and higher for reaction periods of more than about 6 to 10 hours.

Polymerization is preferably performed in an inert (i.e., oxygen free) atmosphere, such as a nitrogen atmosphere. Tolerance to oxygen can be increased by including in the syrup an oxidizable tin compound, as is taught in U.S. Pat. No. 4,303,485. The polymerizations may be conducted in the presence of, or preferably in the absence of, suitable solvents such as ethyl acetate, toluene and tetrahydrofuran which are unreactive with the functional groups of the components of the syrup polymer.

A polymer syrup can be polymerized and crosslinked in air by covering a layer of the photoactive coating with a plastic film that is substantially transparent to UV radiation but impervious to oxygen and irradiating the composition through that film using UV lamps that emit light in the wavelength range corresponding to the absorption maximum of the hydrogen abstracting groups and saturated photoinitiator. Several different commercially available lamps, including medium pressure mercury lamps and low-intensity fluorescent lamps, can be used. The radiation intensity of these lamps is preferably adjusted so that the radiation intensity at the surface of the coating is less than 20 mW/cm$^2$, preferably 0.5 to 6 mW/cm$^2$, each having emission maxima between 200 and 600 nm, preferably between 280 and 400 nm. Maximum efficiency and rate of polymerization are dictated by the relationship between emission properties of the radiation source and absorption properties of the photoactive compounds employed.

Further details of this syrup process can be found in U.S. Pat. No. 5,773,485 (Gaddam et al.).

In some embodiments, the acid functional (meth)acrylate copolymer may be prepared by solution methods. A typical solution polymerization method is carried out by adding the monomers, a suitable solvent, and an optional chain transfer agent to a reaction vessel, adding a free radical thermal- or photo-initiator, purging with nitrogen, and maintaining the reaction vessel at an elevated temperature, typically in the range of about 40 to 100° C. until the reaction is completed, typically in about 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and ethylene glycol alkyl ethers. Those solvents can be used alone or as mixtures thereof.

The extant copolymer, prepared by solution polymerization, is then combined with the photoreactive crosslinking compound of Formula I. The crosslinking compound may be added to the copolymer in amounts of 0.01 to 5 parts by weight, preferably 0.1 to 1 parts by weight, based of 100 parts by weight of acid functional (meth)acrylate copolymer.

The photoinitiator group Z of Formula I is preferably selected as α-cleavage type or a hydrogen-abstraction type photoinitiator to efficiently crosslink the resulting polymer. Preferably the photoinitiator group Z of Formula I is a hydrogen-abstraction-type photoinitiator group.

In some embodiments, the acid functional (meth)acrylate copolymer may be prepared by emulsion processes including batch, continuous or semi-continuous emulsion polymerization processes. In emulsion polymerization a reaction occurs in micelles or emulsion microdrops suspended in aqueous medium. Any heat generated in the microdrops or micelles is quickly moderated by the effect of the heat capacity of the surrounding water phase. Emulsion polymerization proceeds with better control of exothermic reactions, and the resulting adhesive composition is non-flammable as the aqueous medium is the dominant component.

The photoinitiator group Z of Formula I is preferably selected as α-cleavage type or a hydrogen-abstraction-type photoinitiator to efficiently crosslink the resulting polymer. Preferably the photoinitiator group Z of Formula I is a hydrogen-abstraction-type photoinitiator group.

The emulsion polymerization generally comprises the steps of:

(a) making a monomer premix comprising (i) a (meth)acrylic acid ester monomer, (ii) an acid functional monomer; (iii) optionally a polar monomer, (iv) optionally a vinyl monomer, (v) optionally a multifunctional (meth)acrylate; and (vi) optionally a chain transfer agent, (b) combining said premix with a water phase comprising (i) water, (ii) an emulsifier, and (iii)a free radical initiator, preferable a water soluble initiator, (c) concurrently agitating and heating said emulsion to a temperature of about 30° C. to about 80° C., and permitting polymerization of said monomers in the oil-in-water emulsion until a polymeric latex is formed. It will be understood that other mixtures may be used. For example, the acid functional monomer, or other hydrophilic monomers, may be added to the aqueous solution. Once the emulsion mixture is prepared, the monomers may partition between the oil phase and the water phase, according to their respective partition coefficients.

Useful emulsifiers for the emulsion techniques present disclosure include those selected from the group consisting of anionic surfactants, cationic surfactants, nonionic surfactants, and mixtures thereof. A useful range of emulsifier concentration is from about 0.5 to about 8 weight percent, preferably from about 1 to about 5 weight percent, based on the total weight of all monomers of the emulsion pressure sensitive adhesive.

The extant polymer, prepared by emulsion polymerization, is then combined with the photoreactive crosslinking compound of Formula I. The crosslinking compound may be added to the polymer in amounts of 0.01 to 5 parts by weight, preferably 0.1 to 1 parts by weight, based of 100 parts by weight of acid functional (meth)acrylate copolymer. When the photoinitiator group is a hydrogen abstraction-type, the crosslinking compound is generally used in amounts of 0.01 to 0.5 parts by weight, preferably 0.05 to 0.5 parts by weight. When the photoinitiator group is alpha-cleavage-type, the crosslinking compound is generally used in amounts of 0.1 to 3 parts by weight, preferably 0.5 to 2 parts by weight. The photoactive crosslinking agent may be dissolved in a water soluble or water miscible solvent, then added to the emulsion.

Typically the emulsion is combined with the photoreactive crosslinking compound, coated and dried, then exposed to UV radiation to initiate crosslinking. Preferably the photoactive crosslinking compound of Formula I is dissolved in a water-soluble solvent such as ethanol or methanol to facilitate the solubility in the emulsion.

A neutralizing agent may be employed in the preparation of this emulsion copolymer. It may be employed at a level sufficient to neutralize all or a part of the acid groups of the polymer. Neutralization is achieved via the use of an alkali metal hydroxide or a combination of an alkali metal hydroxide with a minor amount of another neutralizing agent. A wide variety of other neutralizing agents may be used as will be understood by those skilled in the art. The selection of the other neutralizing agent, and the amount employed may be varied to achieve a desired result. However, the type and amount selected must not render the adhesive non-dispersible. Preferably ammonium, sodium and potassium hydroxide are used as neutralizing agents.

Another useful method for preparing the acid-functional acrylate copolymers is bulk polymerization. Traditionally, adhesives, such as (meth)acrylics, have been provided in organic solvent for subsequent application. Such adhesives are applied to a substrate and the solvent is then removed. Hot-melt adhesives advantageously reduce or eliminate the use of organic solvents in adhesives and their processing. Hot-melt adhesive systems are essentially 100% solid systems. Usually, such systems have no more than about 5% organic solvents or water, more typically no more than about 3% organic solvents or water. Most typically, such systems are free of organic solvents and water. Advantageously, by reducing the use of organic solvents, special handling concerns associated therewith are also reduced.

Hot-melt processable adhesives have a sufficient viscosity upon melting, such that they can be hot-melt processed (e.g., applied to a substrate). By adjusting the processing temperature and components of an adhesive, the viscosity of the adhesive can be readily tailored for application. For high performance applications (i.e., those requiring relatively strong cohesive strength, such as shear holding strength), some method of increasing the cohesive strength of applied hot-melt adhesives is often needed (e.g., post-crosslinking or moisture-curing).

The acid functional (meth)acrylate copolymer may be prepared by the bulk polymerization methods described in U.S. Pat. No. 6,734,256 (Everaerts et al.), U.S. Pat. No. 4,619,979 (Kotnour et al.), U.S. Pat. No. 4,843,134 (Kotnour et al.) and U.S. Pat. No. 5,753,768 (Ellis), each incorporated herein by reference. The acid functional (meth)acrylate copolymer may be prepared by these described methods, the copolymer combined with the photoactive crosslinking compound, the functionalized copolymer may then be melt processed and coated, and the copolymer then crosslinked by exposure to UV irradiation.

However the acid functional (meth)acrylate copolymer is prepared, it is believed that the aziridine group of the photoreactive crosslinking compound reacts with the pendent acid functional groups of the acid functional (meth)acrylate copolymer to form a carboxyethyleneamino linkage with a pendent photoinitiator group. On exposure to UV irradiation, the photoinitiator group can initiate crosslinking and in the case of syrup polymers, it may also initiate polymerization of the unreacted monomers.

In one embodiment, the intermediate may be of the following structure, with the optional monomer units and unreacted (free) acid functional monomer units not shown.

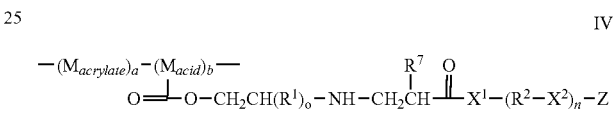

IV where $M_{acrylate}$ represents polymerized monomer units derived from (meth)acrylate monomers, $M_{acid}$ represents polymerized monomer units derived from acid functional monomers, a and b are integers of at least one, such that a+b is polymeric, $X^1$ and $X^2$ are independently —O— or —NH—;

$R^1$ is H or a $C_1$ to $C_4$ alkyl group, and it will be understood that the adjacent methylene may be substituted by one or more $R^1$ groups;

o is 0 to 2;

$R^2$ is a divalent alkylene of 2 to 10 carbon atoms or —$(R^3)_2$C$(CH_2)_m$(CO)O$R^9$—, where m is 0 or 1, $R^3$ is H or a $C_1$ to $C_4$ alkyl group, and $R^9$ is a $C_2$-$C_6$ alkylene;

$R^7$ is H or $CH_3$, n is 0 or 1; and

Z is a photoinitiator group.

It will be further understood that the indicated $R^1$ groups may be on the carbon β to the oxygen atom, as shown, and/or on the carbon α to the oxygen atom, as result of the aziridine ring-opening.

The resultant reaction product of the acid-functional (meth)acrylate copolymer and the photoactive crosslinking compound contains side chains that comprise radiation-sensitive photoinitiator groups activatable by UV radiation, resulting in a crosslinked adhesive product. Although the primary mechanism of crosslinking the acid functional (meth)acrylate copolymer is by UV initiation of the photoinitiator group, it is believed that additional crosslinking may occur through an amine-mediated mechanism from the ring-opened aziridine group. With reference to Formula IV, the amine resulting from the ring opening may form an ionic bond with an adjacent pendent acid group, to ionically crosslink the copolymer.

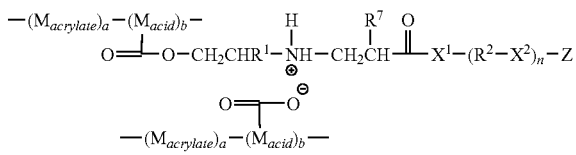

It is further believed that the ionic bond may be subsequently converted to an amide at elevated temperature forming a covalent crosslink from the ionic crosslink. It will be clear that such amide linkages may also result from the reaction of the secondary amine (from the ring-opened aziridine) with a pendent ester group from the ester monomer units.

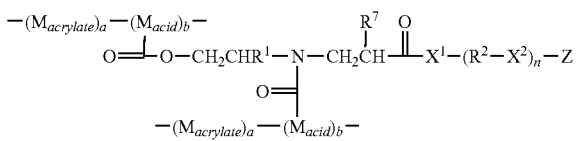

The adhesives may also contain one or more conventional additives. Preferred additives include tackifiers, plasticizers, dyes, antioxidants, and UV stabilizers. Such additives can be used if they do not affect the superior properties of the emulsion pressure sensitive adhesives.

If tackifiers are used, then up to about 40% by weight, preferably less than 30% by weight, and more preferably less than 5% by weight based on the dry weight of the total adhesive polymer would be suitable. Suitable tackifiers for use with (meth)acrylate polymer dispersions include rosin acids, rosin esters, terpene phenolic resins, hydrocarbon resins, and cumarone indene resins. The type and amount of tackifier can affect properties such as contactability, bonding range, bond strength, heat resistance and specific adhesion.

Commercially available tackifiers that are suitable include TACOLYN™ 1070, 5001 and 5002 (aqueous, 55% solids synthetic resin dispersions based on low molecular weight thermoplastic resins, available from Hercules Inc.), SE1055™ (an aqueous dispersion of a rosin ester, available from Hercules Inc.), ESCOREZ™ 9271 (an aliphatic hydrocarbon resin emulsion, available from Exxon), DERMULSENE™ 82, DERMULSENE™ 92, DERMULSENE™ DT or DERMULSENE™ DT50 (aqueous dispersions of modified terpene phenolic resins, available from DRT) and AQUATAK™ 4188 (a modified rosin ester, available from Arizona Chemical Company).

EXAMPLES

Objects and advantages of this invention are further illustrated by the following examples. The particular materials and amounts, as well as other conditions and details, recited in these examples should not be used to unduly limit this invention.

| Materials | |
|---|---|
| Abbreviation or Trade Designation | Description |
| IOA | Isooctyl acrylate |
| 2-OA | 2-Octyl acrylate |

-continued

| Materials | |
|---|---|
| Abbreviation or Trade Designation | Description |
| AA | Acrylic Acid |
| ABP | Acryloylbenzophenone |
| 2-Methylaziridine | Aldrich Chemical, Milwaukee, WI |
| IOTG | Isooctyl thioglycolate, Aldrich Chemical, Milwaukee, WI |
| HDDA | 1,6-Hexanediol diacrylate |
| VAZPIA | prepared as described in Example 1 of U.S. Pat. No. 5,506,279 |

Test Methods:

Peel Adhesion Test [ASTM D 3330/D 3330M-04]

Two 0.5 inch strips of adhesive coated onto Mitsubishi Hostphan™ primed polyester film were adhered to a glass plate by rolling a 2 kg roller onto the tape. The force required to peel the tape was measured in ounces per 0.5 inches with a platen speed of 90 inches per minute. The measurements for the two tape samples were averaged. Peel adhesion data was then normalized to Newtons/decimeter (N/dm) for the tables below.

Shear Strength Test [ASTM D-3654/D 3654M 06 PSTC-7]

A 0.5 inch strip of adhesive coated onto Mitsubishi Hostphan™ primed polyester film was adhered by its adhesive to a stainless steel substrate and cut down to leave a 0.5 inch by 0.5 inch square for room temperature shear testing. A weight of 2 kg was rolled over the adhered portion. A 1000 g load was attached to the tape sample for testing. Each sample was suspended until failure and/or test terminated. The time to failure, as well as the mode of failure, was recorded. Samples were run in triplicate and averaged for the tables below.

Preparation of Aziridine Crosslinking Agents

Preparation of Compound I

Synthesis of 3-(2-methylaziridin-1-yl)propionic acid 2-(4-benzoylphenoxy)ethyl ester (AZBP)

To a 250 mL, one-neck, round bottom flask equipped with a magnetic stirrer were added sodium hydroxide (10.0 g, 0.250 mol) in a water (45 mL)/ethanol (20 mL) solution and 4-hydroxybenzophenone (Alfa Aesar, 50.0 g, 0.250 mol) and the mixture was heated to 55° C. Chloroethanol (Aldrich, 20.3 g, 0.250 mol) in ethanol (25 mL) was then added dropwise to the reaction flask and the mixture heated to 75° C. for 8 hours then cooled to room temperature. The precipitate was collected by filtration, washed with water and recrystallized three times from ethanol/water to obtain 24.4 g of a white solid (4-(2-hydroxyethoxy)benzophenone).

To a 200 mL, one neck, round bottom flask equipped with a magnetic stirrer were added 4-(2-hydroxyethoxy)benzophenone (12.1 g, 5.00 mmol), triethylamine (7.7 mL, 5.57 g, 5.50 mmol), and methylene chloride (60 mL) and the mixture cooled to 0° C. Acryloyl chloride (Aldrich, 4.3 ml, 0.48 g, 5.3 mmol) in 40 mL $CH_2Cl_2$ solution was added over 30 minutes and then the mixture was stirred at room temperature for one hour followed by addition of 50 mL of water. The organic phase was washed 2× with water, dried over $MgSO_4$, filtered and concentrated under vacuum to give 14.8 g of a pale yellow solid (acrylic acid 2-(4-benzoylphenoxy)ethyl ester).

To a 100 mL, one-neck, round bottom flask equipped with a magnetic stirrer were added starting material acrylic acid 2-(4-benzoylphenoxy)ethyl ester (14.75 g, 49.78 mmol), 2-methylaziridine (3.45 g, 54.4 mmol) and methylene chloride (10 mL). The reaction mixture was stirred at ambient temperature overnight. The reaction mixture was then concentrated under reduced pressure for 30 minutes to obtain 17.4 g of Compound I as a viscous light orange oil.

Preparation of Compound II

Synthesis of 3-(2-methylmethylaziridin-1-yl)propionic acid 9,10-dioxo-9,10-dihydro-anthracen-2-ylmethyl ester (AZAN)

To a 100 mL, two neck, round bottom flask equipped with a magnetic stirrer were added triethylamine (2.22 g, 22.0 mmol), $CH_2Cl_2$ (50 mL) and 2-hydroxymethyl-anthraquinone (4.76 g, 20.0 mmol) to form a suspension which was cooled to 0° C. Acryloyl chloride (2.07 g, 22.0 mmol) was added dropwise to the mixture over a period of 10 minutes and the mixture was allowed to stir at ambient temperature overnight. Water (50 mL) was added to the reaction mixture, the organic layer was separated and washed 2× with water, dried over $MgSO_4$, filtered and concentrated under vacuum to give a pale yellow solid. Further purification was completed through column chromatography to give 2.34 g of the product as a pale yellow solid.

To a 100 mL, one-neck, round bottom flask equipped with a magnetic stirrer were added starting material acrylic acid 9,10-dioxo-9,10-dihydroanthracen-2-ylmethyl ester (2.34 g, 8.00 mmol), 2-methylaziridine (1.20 g, 17.6 mmol) and methylene chloride (5 mL). The reaction was stirred at ambient temperature overnight. The reaction mixture was concentrated under reduced pressure for 30 minutes to obtain 2.69 g of Compound II.

Preparation of Compound III

Synthesis of 3-(2-methylaziridin-1-yl)-propionic acid 2-[4-(2-hydroxy-2-methyl-propionyl)phenoxy] ethyl ester (AZHP)

To a 200 mL flask were added triethylamine (5.57 g, 55.0 mmol), methylene chloride (50 mL) and 2-hydroxy-1-[4-(2-hydroxyethoxy)phenyl]-2-methyl-propan-1-one (Aldrich, 11.2 g, 50.0 mmol). The suspension was stirred and cooled to 0° C. Acryloyl chloride (5.18 g, 55.0 mmol) was added dropwise to the reaction mixture over a period of 10 minutes and then the mixture was allowed to stir at ambient temperature overnight. Water (50 mL) was added to the reaction mixture, the organic layer was separated and washed 2× with water, dried over $MgSO_4$, filtered and concentrated under vacuum to give an oil. Further purification was completed through column chromatography to give 5.42 g of colorless liquid (acrylic acid 2-[4-(2-hydroxy-2-methylpropionyl)phenoxy] ethyl ester).

To a 100 mL, one-neck, round bottom flask equipped with a magnetic stirrer were added starting material acrylic acid 2-[4-(2-hydroxy-2-methylpropionyl)phenoxy]ethyl ester (1.12 g, 4.00 mmol), 2-methylaziridine (0.60 g, 8.8 mmol) and methylene chloride (5 mL). The reaction mixture was stirred at ambient temperature overnight. The reaction mixture was then concentrated under reduced pressure for 30 minutes to obtain 1.31 g of Compound III as a viscous oil.

Preparation of Compound IV

Synthesis of 2-methyl-2-[3-(2-methyl-aziridin-1-yl) propionylamino]propionic acid 2-[4-(2-hydroxy-2-methyl-propionyl)phenoxy]ethyl ester (AZAZ)

An approximately 500 mL amber bottle was equipped with a magnetic stir bar and Teflon-lined cap. The threads of the bottle were wrapped with Teflon tape to improve the seal. 2-Acryloylamino-2-methylpropionic acid 2-[4-(2-hydroxy-2-methylpropionyl)phenoxy]ethyl ester (VAZPIA, 42.08 g, 115.8 mmol) was added followed by acetonitrile (100 mL). Next, 2-methylaziridine (10.0 mL 123 mmol) was added. The bottle was tightly sealed with the Teflon-lined metal cap. With stirring, the reaction was heated to 90° C. in an oil bath. After 5 days, the reaction was removed from the oil bath and cooled to room temperature with stirring. A fine white precipitate came out of solution as the reaction mixture cooled. The white solid was collected by vacuum filtration and washed with acetonitrile (75 mL). Residual solvent was removed by high vacuum to provide Compound IV as a white solid: 16.7 g.

TABLE 1

Aziridine crosslinking agents

| | Abbreviation | Molecule Structure |
|---|---|---|
| Hydrogen Abstraction | | |
| I | AZBP | 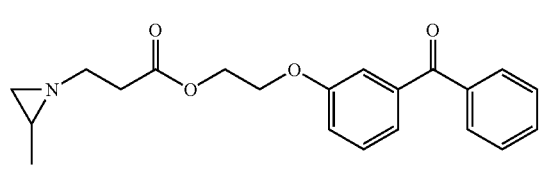 |

TABLE 1-continued

Aziridine crosslinking agents

| | Abbreviation | Molecule Structure |
|---|---|---|
| II | AZAN | |

α-Cleavage

| | | |
|---|---|---|
| III | AZHP | |
| IV | AZAZ | |

Examples 2-4 and Comparative C1 C2 and C3

Preparation of the Syrup Copolymer

A one quart jar was charged with 540 g of isooctyl acrylate (IOA, 90 parts), 60 g of acrylic acid (AA, 10 parts), and 0.24 g of 2,2-dimethoxy-2-phenylacetophenone photoinitiator (Irgacure™ 651, Ciba Specialty Chemicals Inc, 0.04 phr). The monomer mixture was purged with nitrogen for 20 minutes then exposed to low intensity ultraviolet radiation until a coatable syrup copolymer was prepared, after which an additional 0.96 g (0.16 phr) of the photoinitiator was added.

The pre-adhesive polymer syrup was blended with various concentrations of the aziridine crosslinking agent as shown in Table 2. The formulations were then coated between a Mitsubishi Hostphan™ primed polyester film and a Siliconature™ release liner (available from Siliconature S.p.A., Urbano, Italy) at a 2 mil (~50 micrometers) thickness for the syrup pre-adhesive formulations and cured at 400 mJ/cm² The peel and shear data are shown in Table 2.

For comparative purposes, control examples using no crosslinking agent (Example C1), or using 2-(3,4-dimethoxyphenyl)-4,6-bis-trichloromethyl-triazine (using 0.1 phr in Example C2) and 1,6-hexanediol diacrylate (using 0.08 phr) with AZBP (using 0.05 phr in Example C3), as the crosslinking agent was also prepared and tested. Peel Adhesion and Shear Strength were measured for tapes prepared from these adhesive as described in the test methods above.

TABLE 2

| Example | Aziridine Sample | Aziridine crosslinking agent (phr) | Peel Adhesion on Glass (N/dm) 90 in/min | Shear Strength on SS (min) RT | 70° C. |
|---|---|---|---|---|---|
| C1 | | | 81 | 54 (c) | 13 (c) |
| C2 | | | 82 | 7089 (po) | 10,000+ |
| C3 | | | 73 | 1499 (po) | 1708 (c) |
| 2 | AZBP | 0.2 | 77 | 895 (po) | 10,000+ |
| 3 | AZHP | 0.2 | 68 | 2169 (c) | 10,000+ |
| 4 | AZAZ | 0.2 | 59 | 746 (c) | 152 (c) |

Failure mode legend:
(c) stands for cohesive,
(po) stands for pop off.

Examples 5-10, A-B and Comparative C4-C5

Preparation of the Solution Copolymer

2-Octyl acrylate (2-OA, 38.0), acrylic acid (AA, 2.0 g), 2,2'-azobis (2-methylbutyronitrile) (VAZO™ 67, 0.08 g), isooctyl thioglycolate (IOTG, 0.048 g), acrylic acid 3-benzoyl-phenyl ester and ethyl acetate (66.67 g). The bottle was purged with nitrogen for five minutes, sealed, and placed in a water bath maintained at 60° C. for 24 hours.

A series of pre-adhesive copolymer compositions prepared by the solution polymerization were combined with the crosslinking agent as in Table 2. The formulations were then coated on Mitsubishi Hostphan™ primed polyester film at a 1 mil (~25 micrometers) thickness and dried at 70° C. The peel and shear data are shown in Table 3. Incorporation of the crosslinker into the polymer was analyzed by thin layer chromatography as follows. A portion of the dried adhesive was dissolved in ethyl acetate and this ethyl acetate solution examined by TLC (silica gel eluted with ethyl acetate) to show that there was no free crosslinker remaining in the dried polymer. This indicated that the aziridine group of the crosslinker had reacted with the —COOH groups in the polymer and that the crosslinker had thus attached to the polymer.

The same samples were then crosslinked by exposure to UV irradiation at 400 mJ/cm², and the peel and shear tested as shown in Table 3.

For comparative purposes, a control example using no crosslinking agent (Example C4), and a control example using 0.2 phr ABP (Example C5) were also prepared and tested. Peel Adhesion and Shear Strength were measured for tapes prepared from these adhesive as described in the test methods above.

TABLE 3

| Example | Aziridine Sample | Aziridine crosslinking agent (phr) | UV (mJ/cm²) | Peel Adhesion on Glass (N/dm) 90 in/min | Shear Strength on SS (min) RT |
|---|---|---|---|---|---|
| C4-A | | | 0 | 100 | 1 (c) |
| C4-B | | | 400 | 58 | 1 (c) |
| C5-A | | | 0 | 78 | 1 (c) |
| C5-B | | | 400 | 48 | 2774 (po) |
| 5A | AZBP | 0.2 | 0 | 93 | 1 (c) |
| 5B | AZBP | 0.2 | 400 | 58 | 10000+ |
| 6A | AZAN | 0.2 | 0 | 68 | 1 (c) |
| 6B | AZAN | 0.2 | 400 | 52 | 4503 (p) |
| 7A | AZHP | 0.2 | 0 | 86 | 1 (c) |
| 7B | AZHP | 0.2 | 400 | 49 | 41 (c) |
| 8A | AZHP | 1.0 | 0 | 71 | 2 |
| 8B | AZHP | 1.0 | 400 | 43 | 10000+ |
| 9A | AZAZ | 0.2 | 0 | 80 | 1 (c) |
| 9B | AZAZ | 0.2 | 400 | 56 | 6 (c) |
| 10A | AZAZ | 1.0 | 0 | 87 | 1 (c) |
| 10B | AZAZ | 1.0 | 400 | 46 | 542 (po) |

Failure mode legend:
(c) stands for cohesive,
(po) stands for pop off.

We claim:

1. A photoactive crosslinking compound having the general formula:

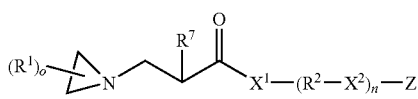

wherein $R^1$ is H or a $C_1$ to $C_4$ alkyl group;
o is 0 to 2;
$X^1$ and $X^2$ are each independently —O— or —NH—;
$R^2$ is a divalent alkylene of 2 to 10 carbon atoms or —$(R^3)_2$C$(CH_2)_m$(CO)O$R^9$—, where m is 0 or 1, $R^3$ is H or a $C_1$ to $C_4$ alkyl group, and $R^9$ is a $C_2$-$C_6$ alkylene;
n is 0 or 1,
$R^7$ is H or $CH_3$; and
Z is a photoinitiator group.

2. The photoactive crosslinking compound of claim 1 wherein Z is a hydrogen abstracting moiety derived from an acetophenone, benzophenone, anthraquinone, 9-fluorenone, anthrone, xanthone, thioxanthone, acridone, dibenzosuberone, benzil, or chromone.

3. The photoactive crosslinking compound of claim 1 wherein Z is a hydrogen abstracting type or an α-cleavage-type photoinitiator group.

4. The photoactive crosslinking compound of claim 1 wherein Z is selected from:

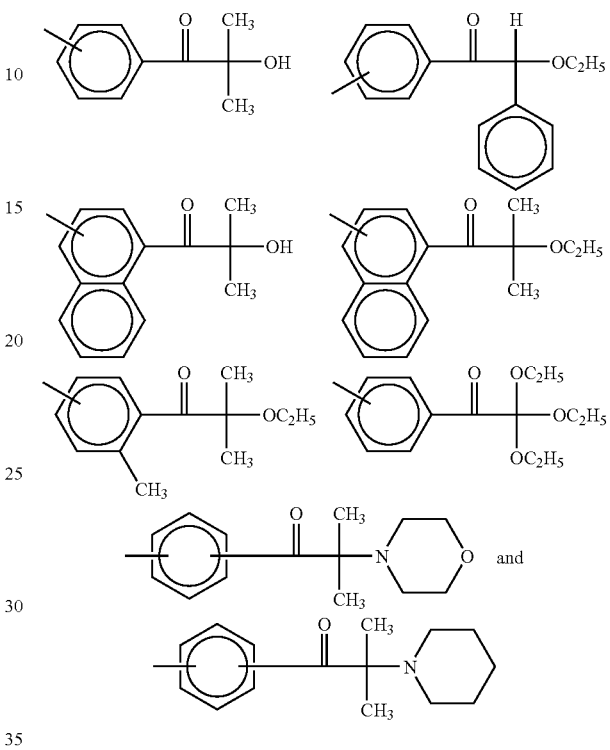

5. The photoactive crosslinking compound of claim 1 wherein Z is derived from a benzophenone, anthraquinone, 9-fluorenone, anthrone, xanthone, thioxanthone, acridone, dibenzosuberone, chromone, flavone, benzyl, and acetophenone compounds having a nucleophilic H—$X^1$—($R^2$—$X^2$)$_n$— group thereon, wherein $X^1$ and $X^2$ are each independently —O— or —NH—; $R^2$ is a divalent alkylene of 2 to 10 carbon atoms or —$(R^3)_2$C$(CH_2)_m$(CO)O$R^9$—, where m is 0 or 1, $R^3$ is H or a $C_1$ to $C_4$ alkyl group, n is 0 or 1, and $R^9$ is a $C_2$-$C_6$ alkylene.

6. The photoactive crosslinking compound of claim 1 of the formula:

II

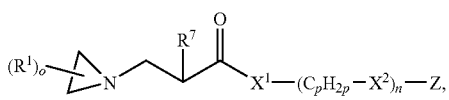

where
$R^1$ is H or a $C_1$ to $C_4$ alkyl group;
o is 0 to 2;
$X^1$ and $X^2$ are independently —O— or —NH—;
p is 2 to 10, preferably 2 to 6,
n is 0 or 1;
$R^7$ is H or $CH_3$; and
Z is a photoinitiator group.

7. The photoactive crosslinking compound of claim 1 of the formula:

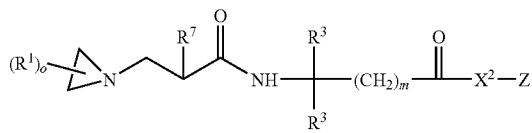

III wherein
R¹ is H or a C₁ to C₄ alkyl group;
o is 0 to 2;
R³ is H or CH₃;
X² is —O— or —NH—;
m is 0 or 1,
R⁷ is H or CH₃; and
Z is a photoinitiator group.

8. The photoactive crosslinking compound of claim 1 wherein Z is selected from:

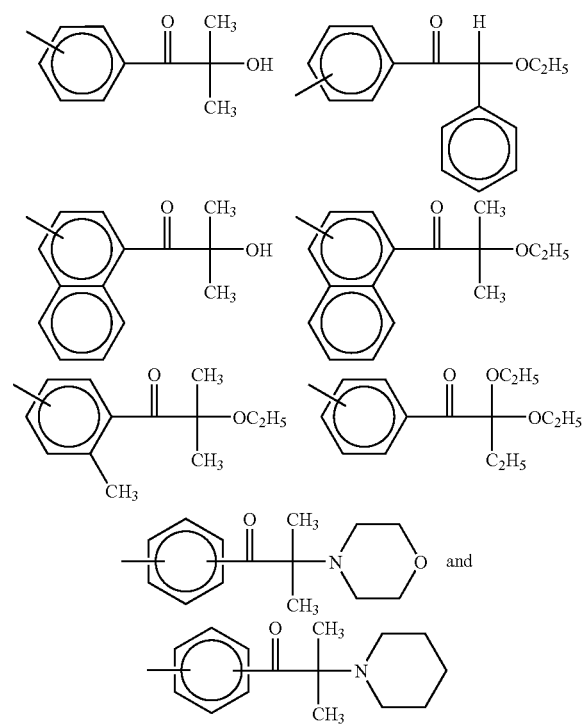

9. The photoactive crosslinking compound of claim 1 of the formula:

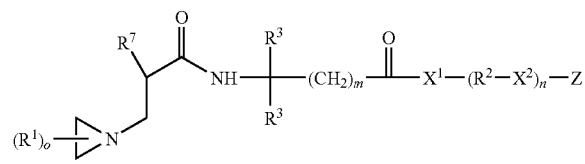

wherein
R¹ is H or a C₁ to C₄ alkyl group;
o is 0 to 2;
R³ is H or CH₃;
X² is —O— or —NH—;
m is 0 or 1,
R⁷ is H or CH₃; and
Z is a photoinitiator group.

10. A method of making the photoactive crosslinking compound of claim 1 comprising the steps of reacting an aziridine compound of the formula:

with an acryloyl compound of the formula

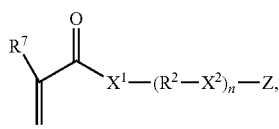

wherein R¹ is H or a C₁ to C₄ alkyl group and o is 0 to 2;
X¹ and X² are each independently —O— or —NH—;
R² is a divalent alkylene of 2 to 10 carbon atoms or —(R³)₂C(CH₂)ₘ(CO)OR⁹—, where m is 0 or 1, R³ is H or a C₁ to C₄ alkyl group, and R⁹ is a C₂-C₆ alkylene;
n is 0 or 1,
R⁷ is H or CH₃; and
Z is a photoinitiator group.

11. A crosslinkable composition comprising an acid-functional (meth)acrylate copolymer and a photoactive crosslinking compound of the formula:

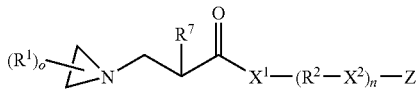

wherein R¹ is H or a C₁ to C₄ alkyl group;
o is 0 to 2;
X¹ and X² are each independently —O— or —NH—;
R² is a divalent alkylene of 2 to 10 carbon atoms or —(R³)₂C(CH₂)ₘ(CO)OR⁹—, where m is 0 or 1, R³ is H or a C₁ to C₄ alkyl group, and R⁹ is a C₂-C₆ alkylene;
n is 0 or 1,
R⁷ is H or CH₃; and
Z is a photoinitiator group.

12. The crosslinkable composition of claim 11 wherein the acid-functional (meth)acrylate copolymer comprises:
   i. 85 to 99 parts by weight of an (meth)acrylic acid ester of non-tertiary alcohol;
   ii. 1 to 15 parts by weight of an acid functional ethylenically unsaturated monomer;
   iii. 0 to 10 parts by weight of a non-acid functional, ethylenically unsaturated polar monomer;
   iv. 0 to 5 parts vinyl monomer; and
   v. 0 to 5 parts of a multifunctional (meth)acrylate;
   based on 100 parts by weight total monomer.

13. The crosslinkable composition of claim 12 comprising 0.005 to 5.0 parts by weight of the photoactive crosslinking compound, relative to 100 parts of the copolymer.

14. The crosslinkable composition of claim 13 wherein said second polar monomer is selected from 2-hydroxyethyl (meth)acrylate; N-vinylpyrrolidone; N-vinylcaprolactam; acrylamide; t-butyl acrylamide; dimethylamino ethyl acrylamide; N-octyl acrylamide; poly(alkoxyalkyl)(meth)acrylates; poly(vinyl methyl ether); and mixtures thereof.

15. The crosslinkable composition of claim 12 wherein said copolymer comprises 1 to 5 parts by weight of acrylic acid and 1 to 5 parts by weight of a polar monomer.

16. The crosslinkable composition of claim 12 wherein said composition is an aqueous emulsion.

17. The crosslinkable composition of claim 12 wherein the acid functional monomer is selected from acrylic acid, methacrylic acid, itaconic acid, fumaric acid, crotonic acid, citraconic acid, maleic acid, oleic acid, β-carboxyethyl(meth)acrylate, 2-sulfoethyl methacrylate, styrene sulfonic acid, 2-acrylamido-2-methylpropane sulfonic acid, vinyl phosphonic acid, and mixtures thereof.

18. The crosslinkable composition of claim 12 comprising 1 to 5 parts of a vinyl monomer selected from vinyl esters, styrene, substituted styrene, vinyl halide, vinyl propionate, and mixtures thereof.

19. The crosslinkable composition of claim 12 with the average number of carbon atoms of the non-tertiary alcohol being from about 4 to about 12.

20. A pressure sensitive adhesive comprising the crosslinked composition of claim 12.

21. The crosslinkable composition of claim 11 wherein said non-tertiary alcohol of said (meth)acrylic acid ester of non-tertiary alcohol is selected from 2-octanol or dihydrocitronellol.

22. An adhesive article comprising the crosslinked composition of claim 20 and a flexible backing layer.

23. An emulsion comprising:
    (a) 30 to about 70 weight percent, based on the total weight of the emulsion, of the crosslinkable composition of claim 22, and
    (b) 30 to 70 weight percent of an aqueous phase comprising a surfactant, based on the total weight of the emulsion.

24. A solution comprising the crosslinkable composition of claim 11 and an organic solvent.

25. A method of preparing a pressure sensitive adhesive comprising combining;
    (a) a copolymer comprising
        i. 85 to 99 parts by weight of an (meth)acrylic acid ester of non-tertiary alcohol;
        ii. 1 to 15 parts by weight of an acid functional monomer;
        iii. 0 to 10 parts by weight of a second, non-acid functional, polar monomer;
        iv. 0 to 5 parts vinyl monomer, with
    (b) a photoactive crosslinking compound of the formula:

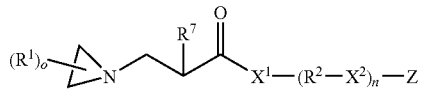

wherein $R^1$ is H or a $C_1$ to $C_4$ alkyl group;
o is 0 to 2;
$X^1$ and $X^2$ are each independently —O— or —NH—;
$R^2$ is a divalent alkylene of 2 to 10 carbon atoms or —$(R^3)_2$C$(CH_2)_m$(CO)O$R^9$—, where m is 0 or 1, $R^3$ is H or a $C_1$ to $C_4$ alkyl group, and $R^9$ is a $C_2$-$C_6$ alkylene;
n is 0 or 1,
$R^7$ is H or $CH_3$; and
Z is a photoinitiator group; and
    (c) heating the mixture, and
    (d) exposing to UV to effect photocrosslinking.

26. Syrup polymer composition comprising:
    a) first component solute polymer comprising:
        i. 85 to 99 parts by weight of an (meth)acrylic acid ester of non-tertiary alcohol;
        ii. 1 to 15 parts by weight of an acid functional monomer;
        iii. 0 to 10 parts by weight of a second, non-acid functional, polar monomer;
        iv. 0 to 5 parts vinyl monomer, and
    b) a second component comprising at least one free-radically polymerizable solvent monomer, and
    an aziridine crosslinking compound of the formula:

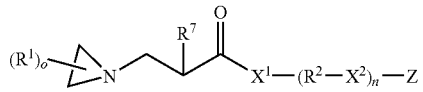

wherein $R^1$ is H or a $C_1$ to $C_4$ alkyl group;
o is 0 to 2;
$X^1$ and $X^2$ are each independently —O— or —NH—;
$R^2$ is a divalent alkylene of 2 to 10 carbon atoms or —$(R^3)_2$C$(CH_2)_m$(CO)O$R^9$—, where m is 0 or 1, $R^3$ is H or a $C_1$ to $C_4$ alkyl group, and $R^9$ is a $C_2$-$C_6$ alkylene;
n is 0 or 1,
$R^7$ is H or $CH_3$; and
Z is a photoinitiator group.

* * * * *

UNITED STATES PATENT AND TRADEMARK OFFICE
CERTIFICATE OF CORRECTION

| | | |
|---|---|---|
| PATENT NO. | : 7,838,110 B2 | Page 1 of 2 |
| APPLICATION NO. | : 12/326213 | |
| DATED | : November 23, 2010 | |
| INVENTOR(S) | : Peiwang Zhu | |

It is certified that error appears in the above-identified patent and that said Letters Patent is hereby corrected as shown below:

First Page, Column 2,
Line 3, under "Other Publications" Delete "Tetraheron," and insert -- Tetrahedron, --.

Column 1,
Line 55, delete "of2" and insert -- of 2 --.

Column 3,
Line 42, delete "$R^3$is" and insert -- $R^3$ is --.
Line 43, delete "x2" and insert -- $X^2$ --.

Column 8,
Line 40, delete "thereof" and insert -- thereof. --.

Column 9,
Line 4, delete "thereof" and insert -- thereof. --.
Line 27, delete "thereof" and insert -- thereof. --.
Line 64, delete "thereof," and insert -- thereof; --.

Column 10,
Line 45, delete "photoinitator" and insert -- photoinitiator --.

Column 12,
Line 28, delete "photoinitator" and insert -- photoinitiator --.
Line 30, delete "photoinitator" and insert -- photoinitiator --.
Line 45, delete "photoinitator" and insert -- photoinitiator --.
Line 47, delete "photoinitator" and insert -- photoinitiator --.

Column 16,
Line 28, delete "06" and insert -- 06, --.

Signed and Sealed this
Fifth Day of July, 2011

David J. Kappos
*Director of the United States Patent and Trademark Office*

Column 18,
Table 1, delete " 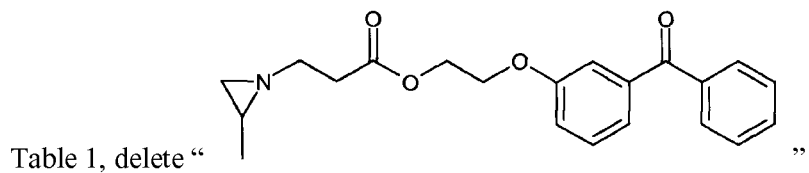 "
and insert -- 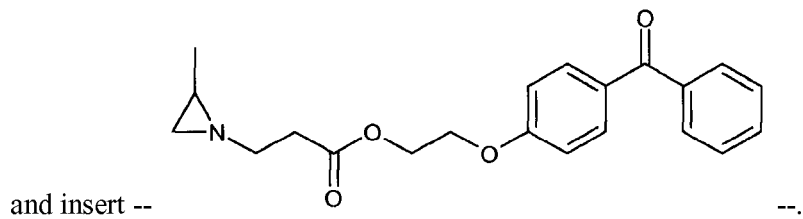 --.
Column 19,
Line 57, delete "mJ/cm²" and insert -- mJ/cm². --.
Column 22,
Line 34, after "  " insert -- . --.
Column 23,
Line 49, after "  " insert -- . --.
Column 24,
Line 65, after "said" delete "second".